United States Patent
Tkaczyk et al.

(10) Patent No.: US 10,531,850 B2
(45) Date of Patent: Jan. 14, 2020

(54) MOBILE X-RAY IMAGING WITH DETECTOR DOCKING WITHIN A SPATIALLY REGISTERED COMPARTMENT

(71) Applicant: General Electric Company, Schenectady, NY (US)

(72) Inventors: John Eric Tkaczyk, Delanson, NY (US); Hao Lai, Niskayuna, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 194 days.

(21) Appl. No.: 15/698,439

(22) Filed: Sep. 7, 2017

(65) Prior Publication Data

US 2019/0069864 A1    Mar. 7, 2019

(51) Int. Cl.
| | | |
|---|---|---|
| *A61B 6/00* | (2006.01) | |
| *A61B 6/04* | (2006.01) | |
| *A61B 6/08* | (2006.01) | |
| *G06T 7/73* | (2017.01) | |

(52) U.S. Cl.
CPC .......... *A61B 6/469* (2013.01); *A61B 6/0407* (2013.01); *A61B 6/0457* (2013.01); *A61B 6/08* (2013.01); *A61B 6/4405* (2013.01); *A61B 6/547* (2013.01); *G06T 7/73* (2017.01); *G06T 2207/10116* (2013.01); *G06T 2207/20092* (2013.01); *G06T 2207/30004* (2013.01)

(58) Field of Classification Search
CPC ....... A61B 6/469; A61B 6/0407; A61B 6/587; A61B 6/025; A61B 6/547; A61B 6/4405; A61B 6/08; A61B 6/0457; G06T 7/73; G06T 2207/30004; G06T 2207/20092; G06T 2207/10116

See application file for complete search history.

(56) References Cited

U.S. PATENT DOCUMENTS

| | | |
|---|---|---|
| 4,105,923 A | 8/1978 | Hynes |
| 6,056,437 A | 5/2000 | Toth |
| 6,310,938 B1 | 10/2001 | Toth et al. |

(Continued)

FOREIGN PATENT DOCUMENTS

| | | |
|---|---|---|
| DE | 102010008552 | 8/2011 |
| DE | 102013219137 A1 | 3/2015 |

(Continued)

OTHER PUBLICATIONS

Fahrig, Rebecca, et al.; "Design, Performance, and Applications of a Hybrid X-Ray/MR System for Interventional Guidance", Proceedings of the IEEE, http://ieeexplore.ieee.org/abstract/document/4446150/, vol. 96, Issue 3, pp. 468-480, Mar. 2008.

(Continued)

*Primary Examiner* — Michael C Bryant
(74) *Attorney, Agent, or Firm* — Fletcher Yoder, P.C.

(57) ABSTRACT

The present approach relates to the use of a spatially registered detector docking compartment to determine source and detector alignment in a patient imaging context. In certain implementations, sensors and/or cameras provide visual data that may be analyzed to determine a spatial relation between an X-ray source and landmarks provided on a patient support surface, where the landmarks have a known spatial relationship to a detector positioned beneath the patient support surface.

19 Claims, 3 Drawing Sheets

(56) References Cited

U.S. PATENT DOCUMENTS

| | | |
|---|---|---|
| 6,327,336 B1 | 12/2001 | Gingold et al. |
| 6,375,354 B1 | 4/2002 | Polkus et al. |
| 6,422,750 B1 | 7/2002 | Kwasnick et al. |
| 6,435,716 B1 | 8/2002 | Polkus et al. |
| 6,439,769 B1 | 8/2002 | Polkus et al. |
| 6,507,638 B2 | 1/2003 | Curtis et al. |
| 6,662,036 B2 | 12/2003 | Cosman |
| 6,702,459 B2 | 3/2004 | Barnes et al. |
| 6,754,306 B2 | 6/2004 | Cho et al. |
| 6,859,521 B2 | 2/2005 | Spahn |
| 6,934,361 B2 | 4/2005 | Ohkoda |
| 7,054,412 B2 | 5/2006 | Scheuering |
| 7,077,568 B2 | 7/2006 | Hornegger |
| 7,344,304 B2 | 3/2008 | Hardesty |
| 7,344,305 B2 | 3/2008 | Kuzmanovic |
| 7,401,977 B2 | 7/2008 | Graumann et al. |
| 7,413,345 B1 | 8/2008 | Spanswick et al. |
| 7,488,108 B2 | 2/2009 | Pommi |
| 7,503,693 B2 | 3/2009 | Jahrling |
| 7,572,057 B2 | 8/2009 | Takekoshi et al. |
| 7,581,885 B2 | 9/2009 | Ertel et al. |
| 7,744,279 B2 | 6/2010 | Heath et al. |
| 7,798,710 B1 | 9/2010 | Barnes et al. |
| 7,869,562 B2 | 1/2011 | Khamene et al. |
| 7,896,547 B2 | 3/2011 | Kito et al. |
| 7,927,014 B2 | 4/2011 | Dehler |
| 7,978,822 B2 | 7/2011 | Windt |
| 7,997,799 B2 | 8/2011 | Jabri et al. |
| 8,172,461 B2 | 5/2012 | Liu et al. |
| 8,331,529 B2 | 12/2012 | Miller et al. |
| 8,690,426 B2 | 4/2014 | Liu et al. |
| 8,696,200 B2 | 4/2014 | Mohr |
| 8,764,291 B2 | 7/2014 | Ruijters |
| 8,821,016 B2 | 9/2014 | Yang et al. |
| 8,867,705 B2 | 10/2014 | Lalena et al. |
| 9,042,519 B2 | 5/2015 | Kuwabara et al. |
| 9,055,922 B2 | 6/2015 | Kuwabara et al. |
| 9,060,731 B2 | 6/2015 | Kuwabara et al. |
| 9,060,738 B2 | 6/2015 | Kuwabara et al. |
| 9,072,440 B2 | 7/2015 | Koishi |
| 9,134,434 B2 | 9/2015 | Niederlohner et al. |
| 9,134,436 B2 | 9/2015 | Kwak et al. |
| 9,155,509 B2 | 10/2015 | Lalena et al. |
| 9,173,628 B2 | 11/2015 | Bouvier et al. |
| 9,179,886 B2 | 11/2015 | Stagnitto et al. |
| 9,265,467 B2 | 2/2016 | Kamiya |
| 9,408,579 B2 | 8/2016 | Yamakawa et al. |
| 9,451,923 B2 | 9/2016 | Hemmendorff et al. |
| 9,474,502 B2 | 10/2016 | Kurze |
| 9,572,544 B2 | 2/2017 | O'Dea et al. |
| 9,795,021 B2 | 10/2017 | Ye et al. |
| 2008/0170669 A1 | 7/2008 | Jensen et al. |
| 2009/0086926 A1 | 4/2009 | Wang et al. |
| 2010/0008473 A1 | 1/2010 | Liu et al. |
| 2010/0019720 A1 | 1/2010 | Liu et al. |
| 2010/0020917 A1 | 1/2010 | Gagliano |
| 2011/0286575 A1 | 11/2011 | Omernick et al. |
| 2012/0014498 A1* | 1/2012 | Akahori ............... A61B 6/025 378/4 |
| 2014/0177798 A1 | 6/2014 | Kitagawa et al. |
| 2014/0205066 A1 | 7/2014 | Kitagawa et al. |
| 2014/0241504 A1 | 8/2014 | Lundstrom et al. |
| 2014/0247918 A1 | 9/2014 | Kang et al. |
| 2014/0314204 A1 | 10/2014 | Sabczynski et al. |
| 2014/0376700 A1 | 12/2014 | Kwak et al. |
| 2015/0049862 A1 | 2/2015 | Ancar |
| 2015/0063538 A1 | 3/2015 | Stevenson |
| 2015/0117601 A1 | 4/2015 | Keeve et al. |
| 2015/0182182 A1 | 7/2015 | Tajima |
| 2015/0190104 A1 | 7/2015 | Exelmans |
| 2015/0223764 A1* | 8/2015 | Kwak ................. A61B 6/4429 378/63 |
| 2015/0228071 A1 | 8/2015 | Jockel et al. |
| 2015/0327830 A1 | 11/2015 | Hu |
| 2015/0359504 A1* | 12/2015 | Zhou .................. A61B 6/547 378/38 |
| 2016/0058403 A1 | 3/2016 | Kim et al. |
| 2016/0213329 A1 | 7/2016 | Dirkes |
| 2016/0287192 A1 | 10/2016 | Cai |
| 2017/0007196 A1 | 1/2017 | Don et al. |
| 2017/0172536 A1* | 6/2017 | Song .................. A61B 6/4417 |
| 2019/0069871 A1 | 3/2019 | Tkaczyk et al. |

FOREIGN PATENT DOCUMENTS

| | | |
|---|---|---|
| DE | 102013221383 A1 | 4/2015 |
| WO | WO2015120926 | 8/2015 |
| WO | WO2016124554 | 11/2016 |

OTHER PUBLICATIONS

Ahmad, Moiz, et al.; "Order of Magnitude Sensitivity Increase in X-ray Fluorescence Computed Tomography (XFCT) Imaging With an Optimized Spectro-Spatial Detector Configuration: Theory and Simulation", IEEE Transactions on Medical Imaging, http://ieeexplore.ieee.org/document/6733374/, vol. 33, Issue 5, pp. 1119-1128, May 2014.

Joyce, Malcolm J., et al.; "Portable, Fast-Neutron Tomography with an Isotopic Source and Organic Scintillation Detectors", IEEE Nuclear Science Symposium and Medical Imaging Conference (NSS/MIC), http://ieeexplore.ieee.org/document/7581956/, Oct. 31-Nov. 7, 2015.

Application No. 18190584.5-1124; EP Search Report dated Feb. 5, 2019; 9 pages.

* cited by examiner

MOBILE X-RAY IMAGING WITH DETECTOR DOCKING WITHIN A SPATIALLY REGISTERED COMPARTMENT

BACKGROUND

The subject matter disclosed herein relates to radiographic imaging, including imaging approaches employing a detector that is not fixed in place.

Digital X-ray imaging systems are becoming increasingly widespread for producing digital data which can be reconstructed into useful radiographic images. In current digital X-ray imaging systems, radiation from a source is directed toward a subject, typically a patient in a medical diagnostic application. A portion of the radiation passes through the patient and impacts a detector that is divided into a matrix of discrete elements, e.g., pixels. The detector elements are read out to generate output signals based upon the quantity or intensity of the radiation impacting each pixel region. The signals may then be processed to generate an image that may be displayed for review.

In certain contexts, a mobile X-ray imaging system may employ a portable detector that is not fixed in position or orientation with respect to the X-ray source. In such contexts, a technician may position the patient and/or portable detector to image the anatomy of interest. In certain circumstances the patient being imaged may be difficult to move or should not be disturbed. Examples of such situations include imaging of newborns or infants in a neonatal intensive care unit (NICU) or of other patients in a critical care type setting, such as a burn unit or intensive care unit (ICU).

In such situations, a mobile imaging system having a portable detector (e.g., a detector that is freely movable relative to the X-ray source) may be employed so that the patient does not have to be moved, and instead the imaging equipment is brought to, and positioned with respect to, the patient. The detector, in such a situation, may be positioned below the patient, such as on a shelf below the patient support surface (e.g., bed) and a single-exposure X-ray image may then be obtained.

In such an approach, only a coarse patient alignment is needed to ensure that the target anatomy is projected onto the detector active area, and will therefore appear in the X-ray image. This coarse alignment may be accomplished based on operator estimation of the placement of the detector based upon a light box shined on the patient during positioning. That is, the path from the X-ray tube head to the projected light box informs the operator about the path of the X-rays and the operator can approximately extrapolate this path to the detector plane.

While this approach may be sufficient for a single-exposure imaging procedure, it is typically not suitable for a tomographic X-ray scan, in which a sequence of offset images are acquired. Such a tomographic scan allows a three-dimensional (3D) view of the patient anatomy to be generated by acquiring this sequence of images (e.g., 5, 10, 15, 20 images) from different views over a limited angular range (e.g., 45°, 60°, 75°, 90°, and so forth). Such a tomographic scan requires additional precise position and orientation information about the source focal spot and detector. However, in contexts where the detector is freely positionable it may not be readily determined if the detector is well-positioned, particularly where the detector is occluded by a table, the patient, blankets covering the patient, or other surface on which the patient is resting cannot be moved.

BRIEF DESCRIPTION

In one embodiment, a method is provided for determining an X-ray scan geometry. In accordance with this method, a portable detector is positioned within a docking compartment provided in a patient support structure. A mobile X-ray imager is positioned with respect to the patient support structure. All or parts of the patient support structure are not fixed with respect to the mobile X-ray imager. The mobile X-ray imager comprises an X-ray source in a known geometric relationship to an optical sensor. A visual image provided by the optical sensor and containing one or more landmarks provided on a patient-facing surface of the patient support structure is analyzed. A source-detector geometry is determined based on a known spatial relationship between the one or more landmarks and the docking compartment. Alternately, the optical sensor or camera can be mounted in a known geometric setting to the X-ray source so the source-detector geometry can be determined by a visual image containing the patient support.

In a further embodiment, a patient support structure is provided. In accordance with this embodiment, the patient support structure comprises: a patient support surface configured to support a patient when in use; a docking compartment configured to hold a portable detector, wherein the docking compartment is provided opposite the patient support surface; and one or more landmarks provided on the patient support surface, wherein the one or more landmarks are spatially registered with the docking compartment.

In an additional embodiment, a method is provided for acquiring X-ray images. In accordance with this method, a portable detector is positioned within a docking compartment provided in a patient support structure. A mobile X-ray imager is positioned with respect to the patient support structure. The mobile X-ray imager comprises: an X-ray source configured to move over a limited angular range during image acquisition; and a collimator configured to control one or both of a size or shape of an emitted X-ray beam. A visual image is acquired using an optical sensor. The visual image includes the X-ray source and one or more landmarks provided on a patient-facing surface of the patient support structure. The visual image of the X-ray source and the one or more landmarks is analyzed to determine a source-detector geometry based on a known spatial relationship between the one or more landmarks and the docking compartment. Operation of one or both of the X-ray source and the collimator is controlled based on the source-detector geometry during an X-ray acquisition.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
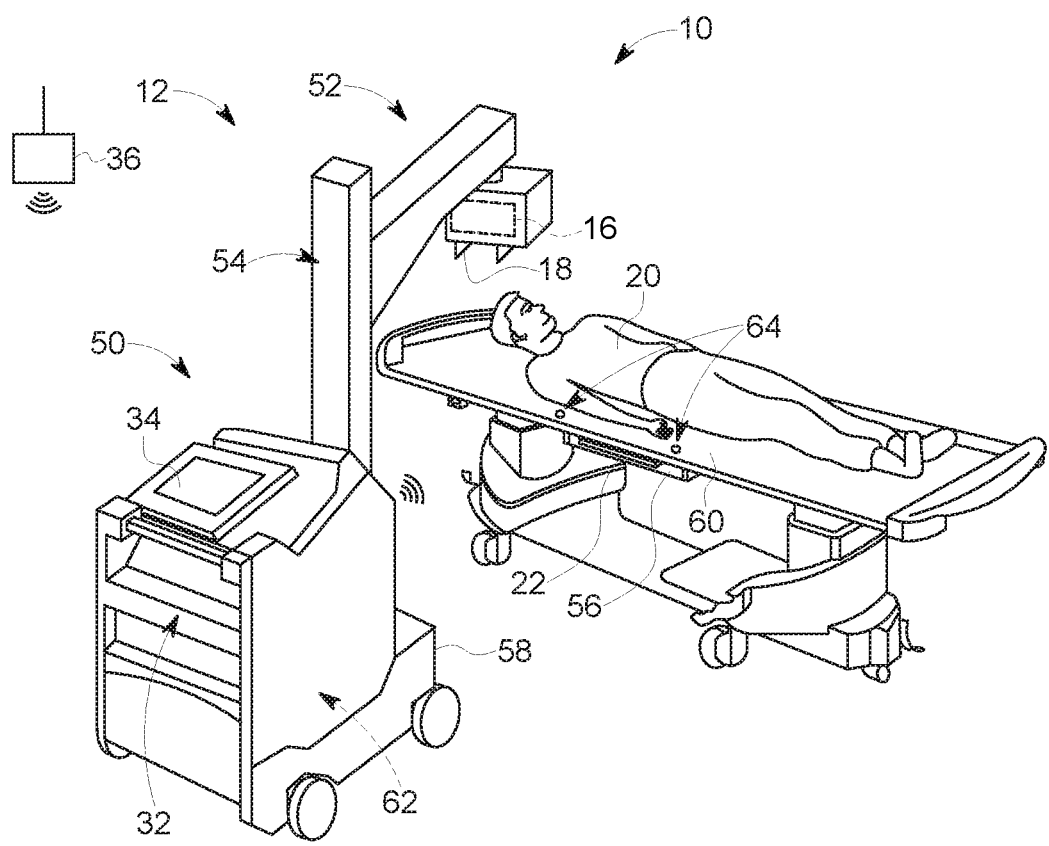
FIG. 1 is perspective view of an embodiment of a mobile X-ray system, equipped in accordance with aspects of the present approach.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present embodiments, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

As discussed herein, various imaging contexts may exist where the patient is not to be moved or disturbed, such as a newborn in a neonatal intensive care unit (NICU) or other patients in intensive care units (ICUs) or burn units. To image such patients a mobile imaging system may be employed, including systems having a portable detector that is detached from the primary imaging base station and generally freely movable with respect to the imager and patient. In such instances, during imaging the detector may be placed below the patient in a compartment of the table or patient support (as opposed to being placed between the patient and patient support surface) and positioned by the operator based on a visual extrapolation of the X-ray path.

While such crude estimation may be sufficient for single exposure images, it is not typically sufficient for tomographic acquisitions, where a series (e.g., 5, 10, 15, 20) of images are acquired of a limited angular range (e.g., 45°, 60°, 75°, 90°, and so forth) so as to all three-dimensional (3D) reconstruction. A reconstruction algorithm creates an accurate 3D view of patient anatomy from data acquired at precisely known locations. In particular, such tomographic imaging processes typically need precise position and orientation information about the source focal spot and detector. The positions and orientations are either precisely controlled motion during acquisition, or are otherwise precisely determined as a result of a registration process. However, simple placement of the detector beneath the patient support surface typically does not provide sufficient position and orientation information for tomosynthesis imaging, potentially missing the anatomy of interest in some number of the views acquired from different angles.

In accordance with the present approach, to address these issues arising from the use of portable detectors in a tomography context, a compartment or chamber is provided beneath a patient support surface (such as a bed surface or table surface) on which the patient rests such that the patient support surface is between the patient and the detector. The compartment is configured to interface or dock with the portable detector such that the detector position with respect to landmarks on the support and the source-detector geometry is thereby determinable or known when the detector is in place. By way of example, in one implementation, housing landmarks are employed to register the position and orientation of the portable detector when docked in the compartment, such as via a provided docking mechanism or structure. In this manner, the problem of occlusion of the detector from camera views is handled by placing the detector and patient anatomy in coordination with the compartment or chamber in which the detector is docked. For example, ArUco markers can be applied on the patient support structure and served as optical landmarks viewed by a camera. Otherwise, methods known in the art of object recognition within images by utilizing color, shape, texture of the patient support can be used to determine the source-detector geometry. Landmarks may incorporate radiopaque materials so that the registration accuracy may benefit from analysis of the features cast in the acquired X-ray images.

With the preceding discussion of the present approach in mind, FIG. 1 depicts an imaging system that may be suitable for implementation of the present approach. In particular an X-ray system is represented and referenced generally by reference numeral 10. In the illustrated embodiment, the X-ray system 10 is a digital X-ray system, such as an X-ray system. The depicted X-ray system 10 is designed both to acquire original image data and to process image data for display in accordance with present techniques. The X-ray system 10 may be a radiographic imaging system, including a system used to image a patient region from multiple angles, such as along a limited angular range so as to generate a three-dimensional representation.

In the embodiment illustrated in FIG. 1, the X-ray system 10 is a mobile imaging system 12 that may be moved to a patient recovery room, an emergency room, a surgical room, a neonatal ward, or any other space to enable imaging of a patient 20 without transporting the patient 20 to a dedicated (i.e., fixed) X-ray imaging room. For the purpose of illustrating the present approach and to provide a real-world context, the present examples primarily focus on mobile X-ray imaging systems employing portable detectors for tomosynthesis imaging, although it should be understood that other imaging approaches using non-mobile systems and/or non-tomosynthesis applications may benefit from the present approach.

In the depicted example, the X-ray system 10 includes a mobile imager or mobile X-ray base station 50 and a portable digital X-ray detector 22 that is freely positionable with respect to the base station 50. In the depicted example, an X-ray base station 50 of the mobile imaging system 12 has a wheeled base 58 to facilitate movement of the station 50.

In the depicted example, a support arm 52 is provided in conjunction with a support column 54 to facilitate positioning of a radiation source 16 and collimator 18 with respect to the patient 20. By way of example, one or both of the support arm 52 and support column 54 may be configured to allow rotation or movement of the radiation source 16 about one or more axes and/or along the lateral extent of the support arm 52, such as to acquire images at different view angles relative to the patient 20. The X-ray source 16 may be provided as an X-ray tube and may be provided in conjunction with a collimator 18 that may be automatically or manually adjusted to shape or limit the X-ray beam incident on the patient 20 and detector 22.

In a mobile imaging context, as discussed herein, the patient 20 may be located on a bed 60 (or gurney, table or any other support) between the X-ray source 16 and the portable detector 22 and subjected to X-rays that pass through the patient 20. During an imaging sequence, the detector 22 receives X-rays that pass through the patient 20 and transmits imaging data to the base station 50. The portable detector 22 in this example is in wireless communication with the base unit 50, though in other examples communication may be completely or partially via a tethered (i.e., cable) connection. The base station 50 houses electronic circuitry 62 that acquires readout signals from the detector 22 and that may be processed to generate diagnostically useful images. In addition, the electronic circuitry 62 may provide and/or and control power to one or both of the X-ray source 16 (i.e., controlling activation and operation of the source 16) and the wheeled base 58 (i.e., a movement system). In the depicted example, the base station 50 also has an operator workstation 32 and display 34 that facilitates user operation of the X-ray system 10. The operator workstation 32 may include a user interface to facilitate operation of the X-ray source 16 and detector 22. In one embodiment, the workstation 32 may be configured to function communicate on or through a network 36 of the medical facility, such as HIS, RIS, and/or PACS. In certain embodiments, the workstation 32 and/or detector 22 may wirelessly communicate with the network 36. Algorithmic computations resulting in determination of source-detector geometry can be done all or in part on the workstation or other server nodes on the network.

As shown in the depicted example the patient support 60 includes a defined docking compartment 56 in which the detector 22 is positioned during imaging. In certain embodiments, the portable detector 22 engages with one or more tracks or docking mechanisms within the compartment 56 (or other docking framework) such that the engagement of the detector 22 within the docking framework rigidly secures the detector 22 in a known position (e.g., x, y, z-coordinates, polar coordinates, or other reference frame data) and/or orientation (e.g., roll, pitch, azimuth) with respect to one or more landmarks 64 (e.g., crosshairs, optical patterns, LED lights, and so forth) that may be visible on the patient facing surface of the support 60. Thus, in this example, the detector 22 is not positioned between the support 60 and patient 20 but under a surface of the support 60, with the position of the detector 22 when so engaged being determinable from the visible landmarks 64 that have a known spatial relationship to the docked detector 22.

Figure 2:
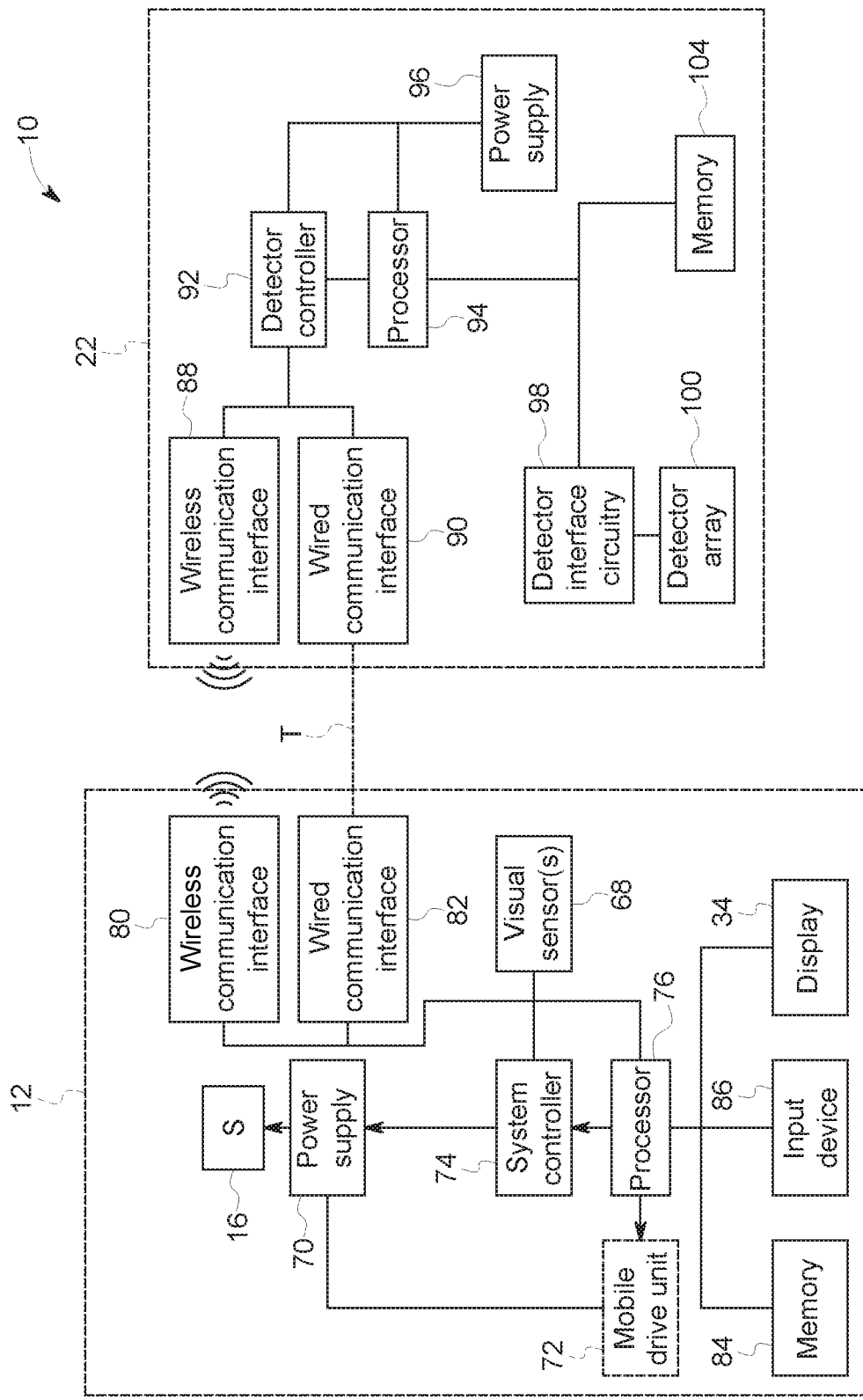
FIG. 2 is a diagrammatical overview of components of an embodiment of an X-ray system in accordance with aspects of the present approach.

While FIG. 1 illustrates schematically aspects of the operation of a mobile X-ray imaging system 10, FIG. 2 diagrammatically illustrates certain components of such a system and their interrelationship.

In the depicted example, the imager system 12 includes the X-ray source 16 connected to a power supply 70 that furnishes both power and control signals for examination sequences. In addition, in mobile imaging systems the power supply 70 may furnish power to a mobile drive unit 72 of the wheeled base 58. The power supply 70 is responsive to signals from a system controller 74. In general, the system controller 74 commands operation of the imaging system to execute examination protocols, such as tomosynthesis examination protocols, and to process acquired image data. In the present context, the system controller 74 also includes signal processing circuitry, typically based upon a general purpose or application-specific circuitry, associated memory circuitry for storing programs and routines executed by the computer, as well as configuration parameters and image data, interface circuits, and so forth. The system controller 74 may include or may be responsive to a processor 76. The processor 76 receives image data from the detector 22 and processes the data to reconstruct an image of a subject. In addition, the processor 76 may calculate or estimate a source-detector geometry (e.g., relative position and orientation), which may be relevant to image acquisition or reconstruction, based on visual sensor inputs and landmarks 64 corresponding to a docked detector 22. With this in mind, the processor 76, in accordance with the present approach may receive inputs from one or more visual sensor(s) 68 (e.g., cameras) of the imager system 12 to facilitate determination of a detector position and/or orientation relative to the source 16, such as during a sequence of image acquisitions for tomosynthesis. In addition, as discussed herein, based upon the relative position of the source and the detector, the processor 76 may control or adjust the radiation source 16 and/or collimator 18 over the course of a sequential X-ray image acquisition, such as may occur in tomosynthesis imaging.

In the implementation shown, the processor 76 is linked to a wireless communication interface 80 that allows wireless communication with the detector 22, e.g., a portable detector. Further, the processor 76 may be linked to a wired communication interface 82 that allows communication with the detector 22 via a tether (e.g., a multi-conductor cable). The imager system 12 may also be in communication with a server providing part or all of the algorithmic computations leading to determination of the source-detector geometry. The processor 76 is also linked to a memory 84, an input device 86, and the display 34. The memory 84 stores configuration parameters, calibration files received from the detector 22, and lookup tables used for image data processing. The input device 86 may include a mouse, keyboard, or any other device for receiving user input, as well as to acquire images using the imager system 12. The display 34 allows visualization of output system parameters, images, and so forth.

The detector 22 includes a wireless communication interface 88 for wireless communication with the imager system 12, as well as a wired communication interface 90, for communicating with the detector 22 when it is tethered to the imager system 12. The detector 22 may also be in communication with a server. It is noted that the wireless communication interface 88 may utilize any suitable wireless communication protocol, such as an ultra wideband (UWB) communication standard, a Bluetooth communication standard, or an 802.11 communication standard, or any other suitable wireless communication standard. Moreover, the detector 22 is coupled or includes a detector controller 92 which coordinates the control of the various detector functions. For example, the detector controller 92 may execute various signal processing and filtration functions, such as for initial adjustment of dynamic ranges, interleaving of digital image data, and so forth. The detector controller 92 is responsive to signals from the system controller 74, as well as the detection circuitry 78. The detector controller 92 is linked to a processor 94 that in turn is linked to a memory 104. The processor 94, the detector controller 92, and all of the circuitry receive power from a power supply 96. The power supply 96 may include a battery. In some embodiments, the detector 22, including the power supply 96, may receive power from the power supply 70 when tethered to the imager system 12.

In the depicted example the processor 94 is linked to detector interface circuitry 98. In one embodiment, the detector 22, which may be used in radiographic, fluoroscopic, tomographic, or other imaging operations, converts X-ray photons incident on its surface to lower energy (e.g., optical light) photons. The detector 22 includes a detector array 100 that includes an array of photodetector elements that generate responsive electrical signals in response to the light photons generated in this manner such that the electrical signals are representative of the number of photons or the intensity of radiation impacting individual pixel regions of the detector surface. Alternatively, the detector 22 may convert the X-ray photons directly to electrical signals (i.e., a direct conversion type detection mechanism). These electrical signals are converted to digital values by the detector interface circuitry 98, which provides the values to the processor 94 to be converted to imaging data and sent to the imager system 12 to reconstruct an image of the features within a subject. Alternatively, the imaging data may be sent from the detector 22 to a server to process the imaging data.

Figure 3:
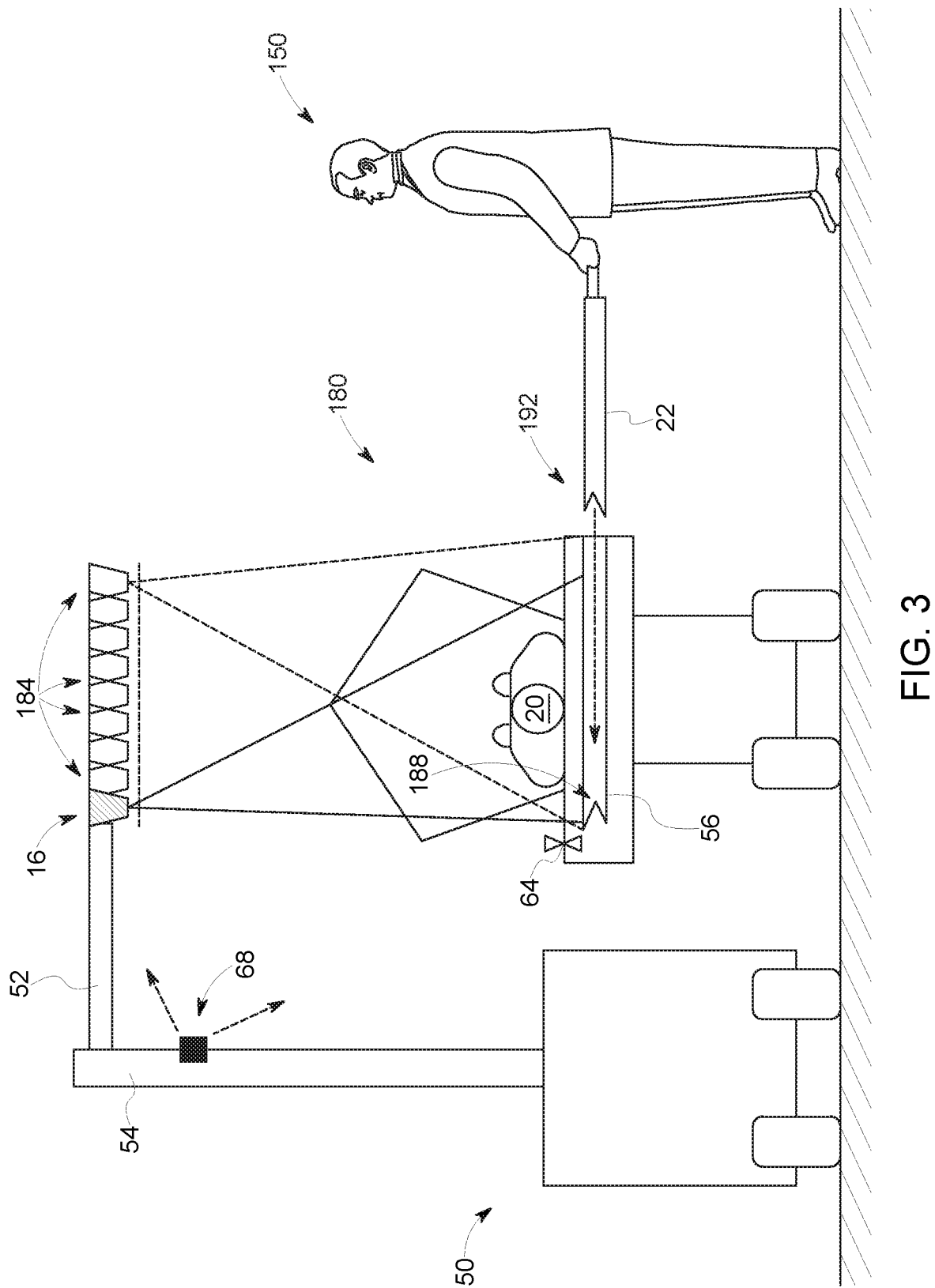
FIG. 3 illustrates schematically aspects of patient and/or detector positioning in accordance with aspects of the present approach.

With the preceding discussion of an imaging system 10 in mind, in accordance with the present approach a portable detector 22 is positioned and oriented with respect to a patient anatomy of interest and an X-ray emission source 16 of a mobile system X-ray imager 12 using a docking compartment 56 associated with externally visible landmark features. Aspects of this approach are depicted graphically in FIG. 3. In the depicted example, the mobile imaging system 50 is configured for a tomosynthesis acquisition. As such, the X-ray source 16 is shown as being movable (here linearly displaced) between a series of view positions 184, each at a different respective view position (i.e., angle) with respect to the patient 20 and detector 22.

A patient 20 to be imaged, here a neonate, is depicted in an incubator 180. In this example, it is undesirable to move the neonate, patient 20, from the incubator for imaging. Likewise, this example illustrates an instance where it may be undesirable to move the patient 20 so as to position a detector 22 between the patient 20 and the support surface. Instead, as discussed herein, a docking compartment 56 is provided in which the detector 22 can be positioned without disturbing the patient. The docking compartment 56 may be configured or structured to mechanically register the detector 22 in a particular manner, such that when inserted properly, the detector 22 is rigidly fixed or held in a known orientation and position. Examples of mechanical structures that may be employed to mechanically register the detector 22 within the compartment include, but are not limited to, the geometry or shape of the compartment 56, one or more guide rails or positioning features within the compartment 56, and/or one or more engagement features or structures (e.g., complementary mating or engagement features 188, 192) provided by detector 22 and compartment 56. Electronic or optical limit switches and/or sensors can inform the system controller 74 that detector engagement is complete. As a result, when the detector 22 is properly fitted in the compartment 56, the detector position and orientation is known with respect to the patient support surface.

In the depicted example an optical sensor 68 (e.g., a camera), which may be provided on the mobile X-ray imaging system 50 as shown, views an alignment feature (e.g., landmark(s) 64, such as cross hairs, LED lights, reflectors, and so forth) on the incubator 180. The optical sensor 68 is mounted to the support column 54 with a known geometry relative to the X-ray source 16. Multiple source locations 184 may be calculated from encoder values of the drive mechanism which translates the source 16. Alternatively the optical sensor 68 may be provided separate from the system but so as to have a view of both the source 16 and landmarks 64. Regardless of the location of the optical sensor(s) 68, the sensor 68 has a view of the source 16 and/or landmarks from a calibrated vantage point that is known or determinable.

As discussed herein, based on the image data acquired from the optical sensor 64, the relative position of the source 16 and the landmark(s) 64 may be determined for a given tomographic image acquisition sequence. Likewise, the position and orientation of the patient 20 may be determined from such optical data. Due to the known relationship between the landmarks 64 and the position and orientation of the detector 22, when the detector 22 is docked within the compartment 56 the relative position and orientation of the source 16 and the detector 22, including the angle of the detector plane relative to the emission focal spot/detector center axis, is also determinable.

For example, in accordance with one embodiment the known vantage of the optical sensor 68 allows relevant tomographic coordinates to be calculated during a scan of the patient 20 through application of one or more monocular or stereoscopic vision analysis routines or algorithms. In other implementations, additional robustness and accuracy may be provided by use of additional cameras, radiopaque markers or other depth sensing sensors. Thus, in these approaches, monocular or stereoscopic analysis of a series of camera image frames allows the source (e.g., tube) focal spot position and the landmark(s) 64 to be registered. Alternately, the camera is in known geometric relationship to the source by virtue of the mounting positions and encoder values of the tomographic drive mechanism.

Thus, in certain implementations, there is a relative position (i.e., three coordinates, x, y, and z) and orientation (i.e., three angles) of the tube focal spot, and compartment relative to some origin point defined for the scan. In addition, as noted above, the patient position may also be observed and, based on the relative source and detector position and orientation, it may be determined if an X-ray projection will fall onto the detector 22 when a directed-tomographic scan is initiated.

In one embodiment, a tomographic scan may be performed that utilizes the positional coordinates determined in this manner configure or adjust the radiation source and collimator opening, thereby allowing X-rays to be incident on the patient anatomy of interest and on the detector's active area. Each sequential exposure in the tomographic scan may be actuated in turn through this mechanism, i.e., collimation may be adapted for each image acquisition to accommodate the relative position and orientation of the source and detector. In addition, the position and orientation data may also be provided to the image reconstruction algorithm to improve or facilitate reconstruction of a 3D view of the patient anatomy.

Technical effects of the invention include the use of a spatially registered detector docking compartment to determine source and detector alignment in a patient imaging context. In certain implementations, sensors and/or cameras provide visual data that may be analyzed to determine a spatial relation between an X-ray source and landmarks provided on a patient support surface, where the landmarks have a known spatial relationship to a detector positioned beneath the patient support surface. This position and orientation information may, in turn be used to control collimation of the X-ray source during a tomographic scan.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for determining an X-ray scan geometry, comprising:
   positioning a portable detector within a docking compartment provided in a patient support structure;
   positioning a mobile X-ray imager with respect to the patient support structure, wherein the mobile X-ray imager comprises an X-ray source in a known geometric relationship to an optical sensor;
   analyzing a visual image generated by the optical sensor of one or more landmarks directly disposed on a patient-facing surface of the patient support structure;
   determining a source-detector geometry based on a known spatial relationship between the one or more landmarks and the docking compartment.

2. The method of claim 1, wherein analyzing the visual image enables determining the source-detector geometry.

3. The method of claim 1, wherein positioning the portable detector within the docking compartment comprises engaging with portable detector with one or more positioning features within the docking compartment.

4. The method of claim 3, wherein the one or more positioning features comprise complementary mating or engagement features.

5. The method of claim 1, wherein the patient support structure comprises a patient bed, a gurney, or an incubator.

6. The method of claim 1, wherein the mobile X-ray imager is configured to move the X-ray source so as to acquire a sequence of images at different views during an acquisition sequence.

7. The method of claim 1, further comprising:
   acquiring the visual image using a camera provided on the mobile X-ray imager.

8. The method of claim 1, further comprising:
   controlling a collimator of the mobile X-ray imager during an image acquisition sequence based on the source-detector geometry.

9. The method of claim 1, further comprising:
   controlling operation of the X-ray source during an image acquisition sequence based on the source-detector geometry.

10. The method of claim 1, further comprising:
    providing the source-detector geometry to an image reconstruction algorithm; and
    reconstructing an image using the image reconstruction algorithm.

11. A patient support structure, comprising:
    a patient support surface configured to support a patient when in use;
    a docking compartment configured to hold a portable detector, wherein the docking compartment is provided opposite the patient support surface; and
    one or more landmarks directly disposed on the patient support surface, wherein the one or more landmarks have a known spatial relationship with the docking compartment.

12. The patient support structure of claim 11, wherein the patient support structure is one of an incubator, a patient bed, or a gurney.

13. The patient support structure of claim 11, further comprising:
    one or more positioning features within the docking compartment.

14. The method of claim 13, wherein the one or more positioning features comprise complementary mating or engagement features.

15. The method of claim 13, wherein the one or more landmarks comprise one or more of crosshairs, radiopaque markers, optical patterns, or LED lights.

16. A method for acquiring X-ray images, comprising:
    positioning a portable detector within a docking compartment provided in a patient support structure;
    positioning a mobile X-ray imager with respect to the patient support structure, wherein the mobile X-ray imager comprises:
       an X-ray source configured to move over a limited angular range during image acquisition; and
       a collimator configured to control one or both of a size or shape of an emitted X-ray beam;
    acquiring a visual image using an optical sensor, wherein the visual image includes the X-ray source and one or more landmarks directly disposed on a patient-facing surface of the patient support structure;
    analyzing the visual image of the X-ray source and the one or more landmarks to determine a source-detector geometry based on a known spatial relationship between the one or more landmarks and the docking compartment; and
    controlling operation of one or both of the X-ray source and the collimator based on the source-detector geometry during an X-ray acquisition.

17. The method of claim 16, wherein positioning the portable detector within the docking compartment comprises engaging with portable detector with one or more positioning features within the docking compartment.

18. The method of claim 17, wherein the one or more positioning features comprise complementary mating or engagement features.

19. The method of claim 16, wherein the patient support structure comprises a patient bed, a gurney, or an incubator.

* * * * *